(12) United States Patent
Briscoe et al.

(10) Patent No.: US 7,909,794 B2
(45) Date of Patent: Mar. 22, 2011

(54) CATHETER WITH AUTOINFLATING, AUTOREGULATING BALLOON

(75) Inventors: Roderick E. Briscoe, Rockford, MI (US); Russell A. Corace, Grand Rapids, MI (US)

(73) Assignee: Medtronic, Inc., Minneapolis, MN (US)

( * ) Notice: Subject to any disclaimer, the term of this patent is extended or adjusted under 35 U.S.C. 154(b) by 1044 days.

(21) Appl. No.: 10/858,685

(22) Filed: Jun. 1, 2004

(65) Prior Publication Data
US 2004/0220522 A1 Nov. 4, 2004

Related U.S. Application Data

(60) Division of application No. 10/235,300, filed on Sep. 5, 2002, now Pat. No. 6,749,583, which is a division of application No. 08/628,763, filed on Apr. 5, 1996, now Pat. No. 6,458,096, which is a continuation-in-part of application No. 08/625,911, filed on Apr. 1, 1996, now Pat. No. 5,807,328.

(51) Int. Cl.
A61M 29/00 (2006.01)
(52) U.S. Cl. ............... 604/96.01; 604/247; 604/537; 606/194
(58) Field of Classification Search ............... 604/96.01, 604/247, 537, 264, 103.07, 103.06, 523, 604/103; 606/192, 194, 195
See application file for complete search history.

(56) References Cited

U.S. PATENT DOCUMENTS

| | | |
|---|---|---|
| 2,078,686 A | 4/1937 | Rowe |
| 3,592,184 A | 7/1971 | Watkins et al. |
| 3,726,283 A | 4/1973 | Dye et al. |
| 3,795,246 A | 3/1974 | Sturgeon |
| 4,029,104 A | 6/1977 | Kerber |
| 4,130,119 A | 12/1978 | Sessions et al. |
| 4,219,026 A | 8/1980 | Layton |
| 4,327,722 A | 5/1982 | Groshong et al. |
| 4,535,757 A | 8/1985 | Webster, Jr. |
| 4,596,548 A | 6/1986 | DeVries et al. |
| 4,598,707 A | 7/1986 | Agdanowski et al. |
| 4,689,041 A | 8/1987 | Corday et al. |
| 4,757,194 A | 7/1988 | Simms |
| 4,813,934 A | 3/1989 | Engelson et al. |
| 4,848,344 A | 7/1989 | Sos et al. |
| 4,850,969 A * | 7/1989 | Jackson ............ 604/96.01 |
| 4,857,054 A * | 8/1989 | Helfer ............ 604/99.03 |
| 4,917,667 A | 4/1990 | Jackson |
| 5,021,045 A * | 6/1991 | Buckberg et al. ............ 604/500 |
| 5,033,998 A | 7/1991 | Corday et al. |
| 5,041,084 A | 8/1991 | DeVries et al. |
| 5,078,681 A | 1/1992 | Kawashima |
| 5,131,429 A * | 7/1992 | Nixon ............ 137/614.2 |
| 5,197,952 A | 3/1993 | Marcadis et al. |
| 5,324,260 A | 6/1994 | O'Neill et al. |
| 5,378,238 A | 1/1995 | Peters et al. |

(Continued)

*Primary Examiner* — Nicholas D Lucchesi
*Assistant Examiner* — Quynh-Nhu H Vu
(74) *Attorney, Agent, or Firm* — Katharine A. Jackson Huebsch; Mike Jaro (57) ABSTRACT

An autoinflating catheter and balloon assembly having an autoregulating structure to prevent overinflation of the balloon as a result of variable fluid flow rates through the catheter lumen. A tight-fitting elastomeric balloon is provided on the distal end of the catheter body, and the assembly is constructed so that at least a portion of the fluid flow through the lumen is directed to the balloon to inflate it. As the balloon is inflated, more and more of the fluid flow through the catheter is discharged from the catheter, thereby preventing overinflation of the balloon.

16 Claims, 4 Drawing Sheets

U.S. PATENT DOCUMENTS

| | | |
|---|---|---|
| 5,385,548 A | 1/1995 | Williams et al. |
| 5,437,632 A | 8/1995 | Engelson |
| 5,454,788 A | 10/1995 | Walker et al. |
| 5,454,789 A | 10/1995 | Burns et al. |
| 5,505,698 A | 4/1996 | Booth et al. |
| 5,792,118 A | 8/1998 | Kurth et al. |
| 5,807,328 A | 9/1998 | Briscoe |
| 6,458,096 B1 | 10/2002 | Briscoe et al. |
| 6,749,583 B2 * | 6/2004 | Briscoe et al. ............ 604/96.01 |

* cited by examiner

CATHETER WITH AUTOINFLATING, AUTOREGULATING BALLOON

CROSS REFERENCE TO RELATED APPLICATIONS

This is a division of application Ser. No. 10/235,300, filed Sep. 5, 2002, which is a division of application Ser. No. 08/628,763, filed Apr. 5, 1996, U.S. Pat. No. 6,458,096, which is a continuation-in-part of application Ser. No. 08/625,911, filed Apr. 1, 1996, U.S. Pat. No. 5,807,328, all of which are incorporated herein by reference in their entirety.

BACKGROUND OF THE INVENTION

1. Field of the Invention

This invention relates to catheter assemblies, and more particularly, to self-inflating or autoinflating balloon catheters within the catheter and balloon assembly, including means for automatically regulating the fluid pressure inside the autoinflating balloon.

2. Description of the Related Art

Catheters have long been used in a wide variety of medical procedures in which the catheter is received in a bodily orifice to conduct fluid by way of the orifice. An example of one such procedure is known as retrograde cardioplegia solution perfusion. The catheter employed is provided with a selectively inflatable cuff or balloon adjacent the distal tip of the catheter. The distal tip is formed with one or more fluid outlets for the discharge of fluid from the catheter assembly. When the distal tip and the balloon are inserted in the coronary sinus and are properly situated, the balloon is inflated to occlude the sinus and to retain the catheter therein. Typically, the catheter and balloon are introduced into the coronary sinus as blood is naturally flowing through it in the opposite direction. Once the balloon has been inflated to occlude the coronary sinus, cardioplegia solution is forced through the catheter to exit through the outlet at the distal tip and perfuse the heart by way of the cardiac veins.

Many different balloon catheter assemblies have been developed for this procedure, but they can be divided between those having manually inflated balloons and those provided with "self-inflating" or "autoinflating" balloons. Manual inflation is accommodated by manufacturing the catheter assembly with a secondary lumen in communication with the interior of the balloon. Autoinflating balloons are automatically inflated by means of a fluid interconnection between the catheter lumen and the interior of the balloon. Most autoinflating balloons are preformed so that the body portion of the balloon extends radially outwardly from the catheter body even in the relaxed condition. However, most manual inflation balloons are formed of an elastomeric material such as silicone so that substantially the entire balloon is tightly received around the body of the catheter in the relaxed position and must be inflated or expanded radially in order to occlude the coronary sinus.

Examples of such catheters are disclosed in U.S. Pat. No. 5,385,548, issued Jan. 31, 1995 to C. R. Williams et al., U.S. Pat. No. 5,197,952, issued Mar. 30, 1993 to S. J. Marcadis et al., and U.S. Pat. No. 4,917,667, issued Apr. 17, 1990 to J. Jackson.

Prior balloon designs may present, one or more of several problems. For example, preformed balloons are typically larger in the relaxed state than the opening of the coronary sinus. Therefore, the balloon is difficult to insert into the coronary sinus and may cause trauma to the tissue as it is inserted. Eliminating the preformed balloon may reduce the trauma the tissue endures during insertion of the balloon. In a catheter having a manually inflated balloon, the balloon may be made of a tightly fitting elastomeric material. Heretofore, however, tightly fitting elastomeric balloons have not been employed in autoinflating catheter balloon assemblies because no effective means were known for controlling the inflation rate of the elastomeric balloon.

SUMMARY OF THE INVENTION

The catheter assembly according to the invention overcomes the problems of the prior art by creating an autoinflating balloon with means for automatically regulating the internal pressure of the balloon in response to the pressure differential between the interior and exterior of the balloon.

The invention comprises a balloon catheter having a catheter body and a balloon secured to the exterior surface of the body. The catheter body has a lumen formed therein with a fluid discharge aperture formed in the body for discharging fluid from the lumen. The balloon is expandable between a relaxed, contracted state and an expanded state in response to a pressure differential between the interior of the lumen and exterior of the balloon. The catheter body is formed with a balloon inflation aperture fluidly interconnecting the lumen and the interior of the balloon. In order to automatically control the inflation rate of the balloon and fluid flow rate of fluid from the catheter, an autoregulation valve is provided on either the balloon or the catheter body. The valve is adapted to seal the fluid discharge aperture and thereby preclude the discharge of fluid from the lumen at a pressure differential lower than a predetermined fluid pressure differential. The autoregulation valve establishes a fluid flow path between the lumen and the fluid discharge at pressure differentials equal to or greater than the. predetermined level.

Preferably, the autoregulation valve is adapted to enlarge the cross-sectional area of the fluid flow path discharge as the fluid pressure differential between the inside and outside of the balloon continues to rise above the predetermined differential.

In one embodiment, the fluid discharge aperture is formed in a fluid flow channel provided in the catheter body adjacent to the balloon. The outer end of the fluid flow channel opens to the exterior of the catheter body. The autoregulation valve comprises an inner end of the fluid flow channel and a portion of the balloon surrounding the inner end of the fluid flow channel so that fluid inside the lumen is prevented from entering the fluid flow channel for discharge from the assembly when the balloon is in the relaxed, uninflated state. The balloon is expandable in response to an increase in fluid pressure in the lumen above the pressure on the exterior of the balloon. Above a predetermined differential, the inner end of the fluid flow channel opens to the interior of the balloon to discharge fluid from the lumen by way of the interior of the balloon and the fluid flow channel.

Preferably, the fluid flow channel comprises a groove formed on the exterior surface of the catheter body wherein the groove is tapered so that the cross-sectional area of the outer end of the groove is greater than the cross-sectional area of the inner end thereof.

Preferably, the distal end of the balloon surrounds the inner end of the groove and is radially expandable and longitudinally extendable so that the portion of the groove which is exposed to the hollow interior of the balloon in the expanded state varies as a function of the radial expansion and longitudinal extension of the balloon. This extension and expansion is in response to increases in fluid pressure inside the balloon.

In an alternative embodiment, the, proximal end of the balloon is secured to the exterior surface of the catheter body and the autoregulation valve comprises a member mounted to the distal end of the balloon and slidably mounted on the distal end of the catheter body. The fluid discharge aperture is formed on the sliding member. A second lumen formed on the sliding member is in fluid communication with the catheter lumen and the fluid discharge apertures. The slidable member is adapted to slide axially relative to the catheter body in response to varying pressure differentials between the interior and exterior of the balloon. The fluid discharge aperture is disposed on the slidable member so that the aperture is closed to fluid communication with the catheter lumen when the balloon is in the relaxed state. The fluid discharge aperture is adapted to be open to fluid communication with the catheter lumen when the fluid pressure differential is sufficient to extend the slidable member a sufficient distance to expose the fluid discharge aperture to the catheter lumen.

In an alternative embodiment, multiple fluid discharge apertures are provided longitudinally along the slidable member whereby the effective area of the fluid discharge aperture will vary with the relative extension of the sliding member in response to increasing fluid pressure within the catheter lumen.

In still another embodiment, the autoregulation valve comprises a one-way valve provided in the catheter lumen. The valve includes a valve member selectively seated in a tapered seat provided within the catheter lumen, proximally of the fluid discharge aperture. The tapered seat is formed with a valve aperture therein in fluid communication with the lumen and having an internal diameter smaller than that of the lumen. A valve member is disposed within the catheter lumen distally of the seat. A valve spring is disposed within the catheter lumen distally of the valve member and adapted to bias the valve member into seating engagement with the seat. The spring is selected to close the valve aperture at fluid pressure differential levels below the predetermined fluid pressure differential and to permit the valve member to be lifted from engagement with the valve seat at fluid pressure differential levels equal to or greater than the predetermined differential. With the valve member so displaced, the fluid discharge aperture is open to the flow of fluid from the lumen.

In yet another embodiment, the autoregulation valve comprises a one-way duckbill valve provided in the catheter lumen. The duckbill valve comprises a pair of tapered valve members extending inwardly from the insides of the lumen. The tapered ends of the valve members abut one another to close the fluid flow path through the lumen. The elastic reaction of the valve members is designed so that the valve members will remain closed until the pressure differential between the interior of the lumen and the exterior of the lumen exceeds a predetermined level. Once this level has been exceeded, the tapered members will part from one another, establishing fluid communication between the fluid discharge aperture and the body of the catheter lumen.

These and other objects, features and advantages of the invention will be apparent from the ensuing description in conjunction with the accompanying drawings.

DETAILED DESCRIPTION OF THE PREFERRED EMBODIMENTS

Figure 1:
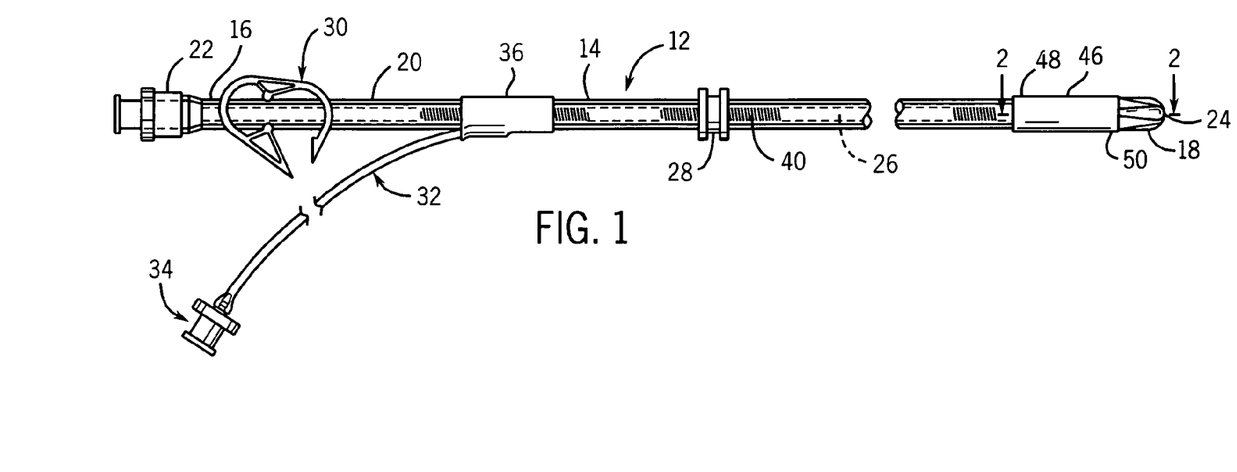
FIG. 1 is a partial side elevational view of an autoinflating, autoregulating balloon catheter assembly according to the invention.

Referring now to the drawings and to FIG. 1 in particular, a catheter assembly 12 according to the invention is shown. In this embodiment, the catheter assembly comprises a catheter 14 having a proximal.end 16, a distal end 18, and a body 20 intermediate the proximal and distal ends. A luer connector 22 is provided on the proximal end 16 and in the first embodiment, the distal end 18 is closed by a rounded tip 24. A lumen 26 extends the length of the catheter 14 from the luer connector 22 to the rounded distal tip 24. A suture collar 28 is provided on the catheter 14 and may be used to secure the catheter 14 to suitable tissue. A clamp 30 is also provided along the length of the catheter so that the lumen 26 may be pinched partially or completely closed between the luer connector 22 and the distal tip 24. A pressure sensing lumen 32 extends from the body 20 of the catheter 14. The pressure sensing lumen 32 has a conventional luer connector 34 provided on the proximal end thereof, and the distal end of the lumen 32 extends to a desired position along the catheter assembly so that the fluid pressure at a desired position inside the catheter 14 may be measured by conventional equipment secured to the luer connector 34. A protective sleeve 36 surrounds the junction between the external portion of the pressure sensing lumen 32 and the body of the catheter 14.

Preferably, the catheter 14 is formed from an elastomeric material, such as silicon, and includes a stiffening member such as a helically coiled wire 40 which is received inside the lumen 26 and extends along a substantial portion of the length of the catheter 14. The use of the autoinflating, autoregulating balloon according to the invention is ideally suited for use with such a catheter structure. However, the invention is by no means limited to such a catheter; any catheter having sufficient rigidity and material compatibility can be used. Similarly, the balloon and catheter assembly is ideally suited for use in a retrograde cardioplegia solution perfusion process. However, the invention is by no means limited to this particular use or method and, in fact, may be used in any process in which a catheter is received in an orifice, an expandable member is provided to occlude the orifice and/or secure the catheter in place and fluid is directed through the catheter.

As seen in FIGS. 1-5, the first embodiment of the autoinflation, autoregulating balloon according to the invention incorporates an expandable member such as a tightly fitting, elastomeric balloon 46 telescopically received on the distal end 18 of the catheter 14. Preferably, the balloon 46 is formed of an elastomeric material such as silicone. However, other elastomeric materials such as a styrene-based polymer like Krayton Rubber™, available from Shell Chemical Co. of Houston, Tex. or a siliconized Krayton Rubber such as C-FLEX™ available from Consolidated Rubber Technologies of largo, Florida may also be used according to the invention. The proximal end of the balloon 46 is secured to the outside surface of the catheter 14 by an adhesive or other conventional means to create a proximal retention collar 48. However, the distal end 50 of the balloon 46 is not secured to the outside surface of the catheter 14. In the relaxed state, the distal end 50 of the balloon 46 tightly surrounds the catheter. At least one balloon aperture 52 is formed in the catheter 14 intermediate the proximal retention collar 48 and distal end 50 to fluidly interconnect the lumen 26 and the interior of the balloon. This balloon aperture 52 is the only aperture formed in the distal end of the catheter 14.

Figures 2, 3:
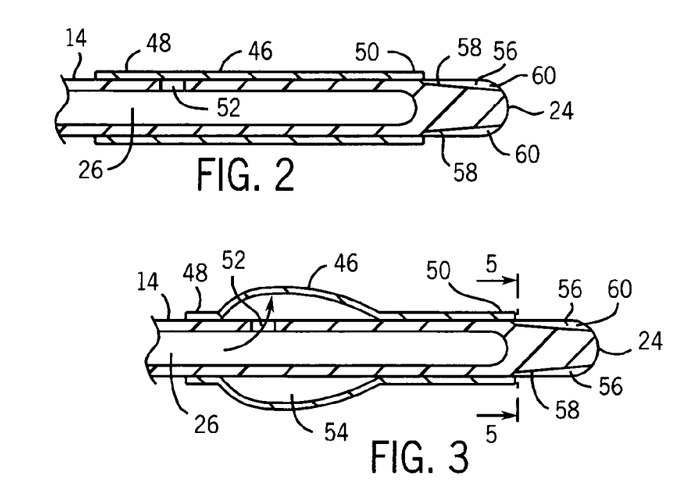
FIG. 2 is a longitudinal sectional view of the distal end portion of the catheter assembly of FIG. 1, taken along line 22 thereof and showing the balloon of the assembly in the unexpanded or relaxed state.
FIG. 3 is a view similar to FIG. 2, but showing the balloon in a partially expanded state.

Pressurized fluid, such as a cardioplegia perfusion solution, is supplied to the catheter assembly through conventional equipment attached to the luer connector 22. The solution flows from the proximal end 16 to the distal end 18 of the catheter. As fluid flows distally through the lumen 26, it exits the lumen and enters the balloon 46 through the balloon aperture 52. The balloon will inflate depending upon the pressure differential between the fluid pressure on the inside of the lumen 26 and that outside the balloon. Initially, the fluid pressure inside the lumen is at atmospheric pressure. As pressurized fluid is supplied to the interior of the lumen, the pressure will rise. The balloon will not begin to expand until a positive pressure differential is created between the fluid pressure on the interior of the lumen and on the exterior of the balloon. More precisely, the balloon will not expand until the pressure inside the lumen and inside the balloon exceeds the pressure outside the balloon and exceeds the elastomeric resistance of the radial expansion of the balloon material. This pressure differential will be referred to as the "predetermined fluid pressure differential."

The balloon aperture 52 is preferably provided adjacent to the proximal retention collar 48. Therefore, once the pressure differential exceeds the predetermined fluid pressure differential, pressurized fluid is forced from the lumen 26 through the aperture 52, and the body of the balloon 46 is expanded radially. Testing has shown that the balloon 46 will also extend longitudinally simultaneous with the radial or hoop expansion. FIG. 3 depicts the balloon 46 in the partially expanded state wherein only the proximal half of the balloon 46 has expanded radially and the balloon 46 has extended longitudinally a short distance in response to the pressurized fluid received therein through the lumen 26 and balloon aperture 52.

The distal end 18 of the catheter 14 includes at least one channel or groove 56 formed for the discharge of fluid from the catheter. In the preferred embodiment, four grooves 56 are formed in the exterior surface of the catheter body, and the grooves 56 taper so that the cross-sectional area of each groove increases from the proximal end of the groove 58 to the distal end of the groove 60. Preferably, the distal end 50 of the balloon 46 terminates at or proximally from the proximal end 58 of the groove 56 when the balloon 56 is in the relaxed, uninflated state. In this position, no fluid communication exists between the grooves 56 and the interior of the balloon 46. As pressurized fluid flows through the lumen 26 into the balloon 46, the balloon expands radially and extends longitudinally. As the balloon 46 extends longitudinally, the distal end 50 of the balloon begins to overlap the proximal ends 58 of the groove 56. In the intermediate state, as seen in FIG. 3, the distal end 50 of the balloon partially overlaps the groove 56. However, at least a portion of the balloon proximal of the groove 56 still tightly surrounds the body of the catheter 14. In this intermediate state, no fluid flow path is established through the balloon 46 or catheter 14, and therefore, all of the fluid flow is contained inside the balloon 46 and catheter lumen 26.

Figures 4, 5:
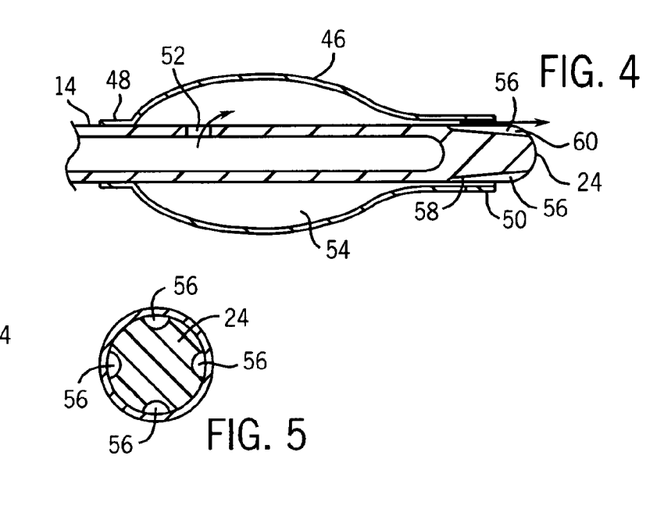
FIG. 4 is a view similar to FIGS. 2 and 3, but showing the balloon in the fully expanded state.
FIG. 5 is a cross-sectional view of the distal end portion of the catheter assembly taken along line 5-5 of FIG. 3.

With the continued increase in fluid pressure differential, the balloon 46 will eventually expand radially and extend longitudinally a sufficient distance so that both the distal end 50 and the expanded body of the balloon 46 will overlap the groove 56 so that fluid will flow from the interior of the balloon, through the groove 56 to the exterior of the catheter assembly 12. If the fluid flow rate through the catheter increases, the cross-sectional area of the exit aperture of the flow path will increase as the distal end of the balloon continues to extend longitudinally along the length of the tapered grooves 56. The flow rate through the balloon 46 may increase so great so that the distal end 50 of the balloon 46 will expand radially outwardly from the catheter 14 thereby creating a fluid flow path around substantially the entire periphery of the catheter 14. As is evident, the fluid pressure on the interior of the balloon will remain substantially constant for a wide range of fluid flow rates through the catheter assembly because of the varying cross sectional area of the fluid discharge aperture.

In the preferred embodiment, substantially no fluid outlet from the catheter assembly 12 exists until the predetermined fluid pressure differential is exceeded and the balloon has reached a certain inflation. However, it is possible to modify this structure to provide a relatively small diameter fluid aperture on the catheter body or overlap the distal end of the balloon over the groove so that a small amount of fluid will flow from the catheter assembly prior to full inflation of the balloon. In this embodiment, as pressurized fluid is provided in the lumen 26, some of the fluid will inflate the balloon and some will pass through the fluid aperture. It may take longer for the predetermined fluid pressure differential level to be exceeded because some of the fluid pressure on the interior of the lumen 26 and balloon is allowed to escape through the aperture on the catheter body. When the balloon is fully inflated and the flow path to the groove established, a greater volume of fluid will be discharged from the assembly.

In the preferred embodiment, the balloon 46 and catheter 14 are structured so that the internal pressure and resulting inflation of the balloon can be controlled for a wide range of fluid flow rates through the catheter assembly. In retrograde cardioplegia perfusion processes, it is desired to create an autoinflating balloon that cannot be over-inflated over a broad range of fluid flow rates. By controlling the internal pressure and resulting inflation of the balloon 46 for a wide range of flow rates of fluid from the catheter, the catheter assembly according to the invention achieves this goal. Utilizing the catheter structure according to the invention, significant variances in the flow rate will result in less dramatic variances for the relative inflation of the balloon, thereby decreasing the chance for tissue damage as a result of balloon over-inflation.

In one test of a catheter assembly as described above, a fluid flow rate through the lumen of less than 100 ml/min creates an initial pressure differential between the interior of the balloon and the exterior of the balloon of less than 30 millimeters Hg. As the internal balloon pressure continues to build and the pressure differential increases, the balloon expands radially and extends longitudinally, eventually establishing the fluid interconnection between the interior of the balloon and the exterior of the catheter assembly. For fluid flow rates in the range of 100 ml/min to 300 ml/min a pressure differential between the interior of the balloon and the exterior is in the range of 30 millimeters Hg to 50 millimeters Hg. As seen by these test results, a three times increase in the flow rate (i.e., over 200 ml/min) results in less than a two times increase in the pressure differential (i.e., less than 20 mm Hg) between the interior and exterior of the balloon, thereby making over-inflation of the balloon more and more difficult as a result of the autoregulating structure of the catheter assembly according to the invention. In effect, the inflation pressure of the balloon is autoregulated by, the structure of the catheter assembly. As the fluid flow rate through the catheter assembly becomes larger and larger, the distal end 50 of the balloon will expand further radially and longitudinally providing a larger fluid flow outlet from the catheter assembly so that more fluid may escape therefrom. The relative size of the fluid flow outlet varies directly as a function of the pressure differential between the fluid pressure inside and outside the balloon.

Figure 6:
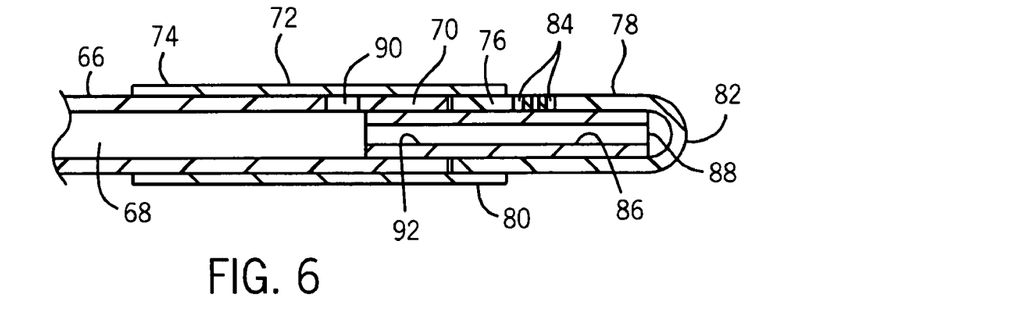
FIG. 6 is a view similar to FIG. 2, but showing the distal end portion of a second embodiment of the autoinflating, autoregulating balloon catheter assembly according to the invention with the balloon of the assembly in the unexpanded or relaxed state.
Figure 7:
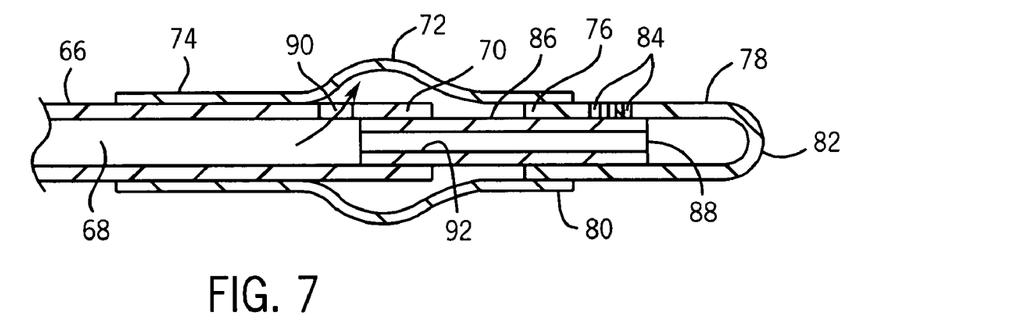
FIG. 7 is a view similar to FIG. 6, but showing the balloon in a partially expanded state.
Figure 8:
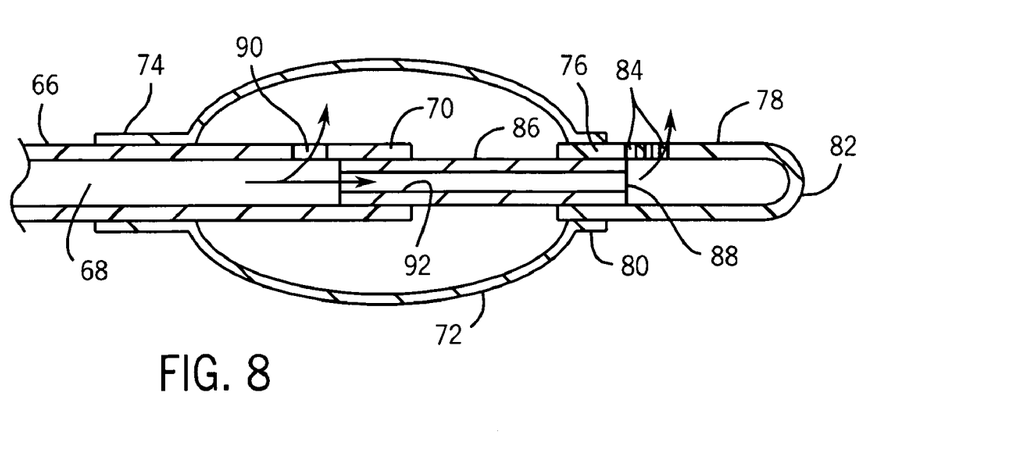
FIG. 8 is a view similar to FIGS. 6 and 7, but showing the balloon in the fully expanded state.

A second embodiment of the autoinflating, autoregulating catheter assembly according to the invention is seen in FIGS. 6-8. In this embodiment, the catheter 66 has a lumen 68 extending from the luer connector (not shown) to the distal tip 70 of the catheter. The proximal end of an elastomeric balloon 72 is securely mounted to the exterior surface of the catheter 66 by conventional means to create a proximal retention collar 74. The distal end of the balloon is securely mounted to the proximal end 76 of a sliding member 78 by conventional means to create a distal retention collar 80 for the balloon 72. The sliding member 78 is substantially tubular in cross section and has a closed, distal end 82 and at least one fluid outlet aperture 84 provided a spaced distance from the proximal end 76. The sliding member 78 is telescopically and slideably received onto the distal end 88 of a guide member 86. The proximal end 92 of the guide member 86 is securely mounted to the interior of the catheter distal tip 70.

In the relaxed condition as seen in FIG. 6, the elastomeric balloon 72 is tightly received around the periphery of the catheter 66 and sliding member. 78. Also, the sliding member 78 is fully retracted with respect to the catheter 66 and guide member 86 so that the distal end 70 of the catheter 66 is closely adjacent to the proximal end 76 of the sliding member 78. As pressurized fluid is provided to the catheter lumen 68 in a sufficient amount to create a pressure differential whereby the internal pressure inside the lumen exceeds the external fluid pressure, the fluid passes through the balloon aperture 90 into the balloon 72 thereby causing the balloon 72 to expand radially. Similarly, the pressurized fluid acts on the closed hollow interior of the sliding member 78 and causes the sliding member 78 to slide along the guide member 86 and the distal portion of the balloon 72 to extend longitudinally relative to the catheter 66. In the interim state as seen in FIG. 7, pressurized fluid cannot yet be discharged from the catheter because the fluid outlet apertures 84 are substantially covered by the guide member 86. As the pressure differential continues to rise, the balloon 72 will continue to expand radially and extend longitudinally. Eventually, as seen in FIG. 8, the balloon and sliding member 78 will have extended along the guide member 86 a sufficient distance so that at least one of the fluid outlet apertures 84 is fluidly interconnected with the catheter lumen 68. Therefore, pressurized fluid will be discharged through the outlet aperture 84 while simultaneously maintaining the inflation of the balloon 72. In the event that the pressure differential drops below the predetermined fluid pressure differential, the elasticity of the balloon will retract the sliding member 78 and balloon 72 thereby covering some or all of the exposed fluid outlet apertures 84. As the cross-sectional area of the fluid outlet apertures are successively reduced, the pressure inside the balloon 72 and lumen 68 will rise until the predetermined fluid pressure differential is again exceeded, thereby causing the sliding member 78 to slide along the guide member 86 a sufficient distance so that some or all of the fluid outlet apertures 84 are again in fluid communication with the lumen 68.

Over-inflation of the balloon 72 for a wide range of fluid flow rates is prevented by the location of additional fluid outlet apertures 84 on the sliding member 78. Once the balloon 72 and sliding member 78 are extended a sufficient distance, fluid will flow through at least one of the outlet apertures. As the internal pressure inside the balloon 72 and catheter lumen 68 continues to build, the balloon and sliding member 78 will extend further, longitudinally. If multiple, balloon apertures 84 are aligned longitudinally along the length of the sliding member, further extension of the sliding member along the guide member 86 will result in increasing the effective size of the fluid flow outlets by exposing additional fluid apertures 84 for the discharge of fluid from the lumen 68. As the excessive pressure is exhausted from the lumen, the elasticity of the balloon 72 will retract the sliding member 78 relative to the guide member 86 thereby covering up some or all of the fluid apertures 84. This structure creates a dynamic, autoregulating catheter and reduces the chances for over-inflation of the balloon, potentially damaging the surrounding tissue.

It is evident that the catheter assembly according to the second embodiment may be customized and modified for a variety of different procedures. For example, the number and diameter of the fluid outlet apertures 84 may be varied to create different, dynamic responses of the sliding member 78 to the changes in the fluid pressure differential between the interior and exterior of the catheter 66. For example, successively increasing the diameter of the fluid outlet apertures from the distal end to the proximal end will provide effective means to prevent over-inflation of the balloon by providing larger and larger fluid outlets. The larger fluid outlets would be successively fluidly interconnected to the lumen as the sliding member and balloon extend further, longitudinally along the guide member 86. The diameter of the fluid apertures 84, the elasticity of the balloon material, the diameter of the balloon inflation apertures 90, and the length of the guide member 86 may be varied to customize each particular application of the catheter assembly according to the invention. These multiple variables provide a wide variety of means for altering the structure and performance of the catheter assembly according to the invention.

In the second embodiment, no fluid exits the catheter until a prescribed fluid pressure is established inside the catheter. Similar to the first embodiment, the second embodiment may be varied to include a relatively small fluid outlet on the sliding member so that some fluid will be constantly discharged from the catheter regardless of the position of the sliding member relative to the guide member.

Figure 9:
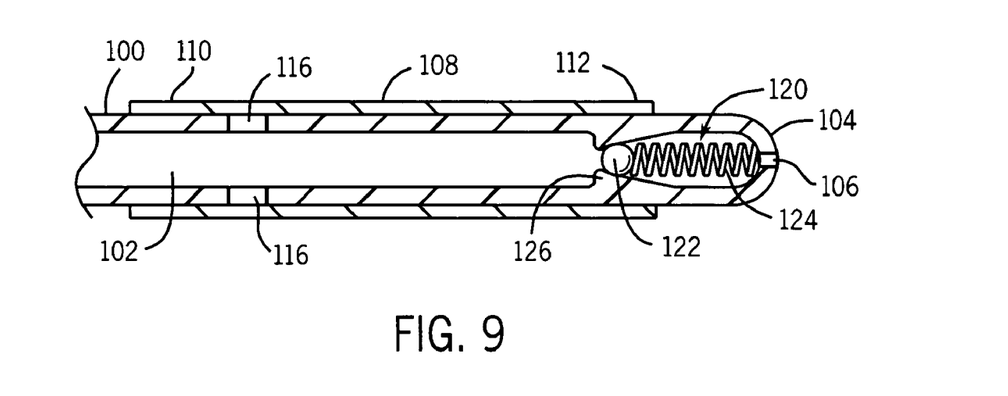
FIG. 9 is a view similar to FIG. 2 or FIG. 6, but showing the distal end portion of a third embodiment of the autoinflating, autoregulating balloon catheter assembly according to the invention with the balloon of the assembly in the unexpanded or relaxed state.
Figure 10:
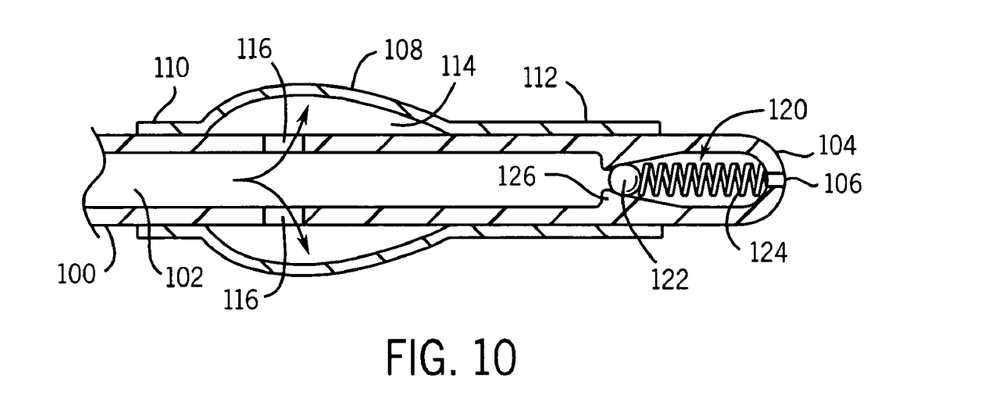
FIG. 10 is a view similar to FIG. 9, but showing the balloon in a partially expanded state.
Figure 11:
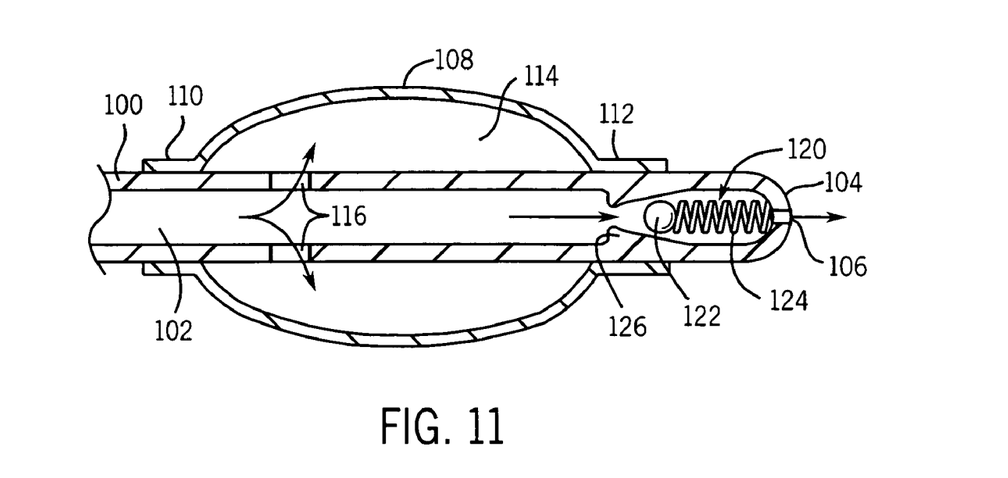
FIG. 11 is a view similar to FIGS. 9 and 10, but showing the balloon in the fully expanded state.

A third embodiment of the autoregulating, autoinflation assembly according to the invention is seen in FIGS. 9-11. In this embodiment, the catheter 100 has a lumen 102 extending from a luer connector (not shown) provided on the proximal end of the catheter 100 and at least one fluid outlet aperture 106 provided on the distal end of the catheter 104. A balloon 108 formed of a tightly fitting, elastomeric material is mounted to the exterior surface of the catheter 100 by conventional means such as adhesive to create a proximal retention band 110 and distal retention band 112. The interior 114 of the balloon 108 is fluidly connected to the lumen 102 by at least one balloon aperture 116. Therefore, as pressurized fluid is supplied to the lumen 102, at least a portion of that fluid is received in the balloon 108 through the apertures 116 resulting in radial expansion of the balloon 108 from the catheter 100.

Internal valve means 120 are provided in the distal end 104 of the catheter 100 intermediate the fluid outlet aperture 106 and the balloon apertures 116. In this embodiment, the internal valve means 120 comprises a valve member or ball 122 which is biased proximally, away from the fluid outlet apertures 106 by a spring 124. A tapered valve member seat 126 or shoulder is provided inside the lumen 102 of the catheter. The valve member seat 126 is preferably integrally formed with the catheter 100 and defines an opening having a diameter slightly smaller than that of the ball 122. The spring 124 biases the ball 122 against the valve member seat 126 to effectively seal the fluid outlet apertures 106 from the remainder of the catheter lumen 102.

In use, pressurized fluid is provided to the lumen 102, and the spring 124 is selected so that the ball 122 will remain biased against the seat 126 until a predetermined fluid pressure differential level is reached. This pressure differential is more than that required to begin the radial expansion of the balloon 108. Therefore, as pressurized fluid is provided in the lumen 102, the balloon expands radially until the predetermined pressure differential is exceeded and the fluid pressure is sufficient to overcome the bias of the spring 124. Once this point is reached, as seen in FIG. 11, the ball 122 will be retracted from the seat 126 and fluid will begin to flow from the lumen 102 through the seat 126 and out the fluid outlet aperture 106. However, this condition will only continue provided that the pressure differential exceeds the predetermined fluid pressure differential and the fluid pressure inside the lumen maintains sufficient pressure to overcome the bias of the spring 124. In the event that the fluid pressure differential drops below this predetermined differential level, the spring 124 will again force the ball 122. against the seat 126, stopping the flow of fluid from the distal end 104 of the catheter 100. Therefore, all fluid flow inside the lumen will be directed to the balloon 108 through the balloon apertures 116 until sufficient pressure differential exists to overcome the bias of the spring 124.

Once again, the strength of the spring, the size of the balloon apertures 116 and the elasticity of the balloon material may all be varied and coordinated to create numerous modifications and customizations of the autoinflating, autoregulating catheter assembly. This structure may be further modified by using a valve member of a different construction. For example, a truncated cone-shaped valve member could be substituted for the ball valve member. Other shapes for the valve member could be substituted depending upon the application.

Similar to the earlier embodiments, this embodiment of the autoregulating catheter assembly incorporates means for maintaining the fluid pressure and inflation of the balloon over a wide range of fluid flow rates through the catheter assembly. In this embodiment, the valve member seat 126 is tapered. Therefore, once the pressure differential exceeds the predetermined fluid pressure differential, the ball will be moved distally with respect to the valve seat 126, thereby establishing fluid flow communication between the interior of the lumen 102 and the aperture 106. As the pressure inside the lumen continues to rise, the ball 122 will be displaced further distally along the length of the tapered seat, thereby increasing the effective cross-sectional area of the flow path through the seat. As the effective cross-sectional area increases for increasing fluid pressure differential above the predetermined fluid pressure differential, the inflation of the balloon will remain substantially constant. As the fluid pressure drops, the spring 124 will bias the ball proximally, toward the narrow end of the tapered valve seat 126, once again, maintaining the inflation rate and pressure inside the balloon.

Figure 12:
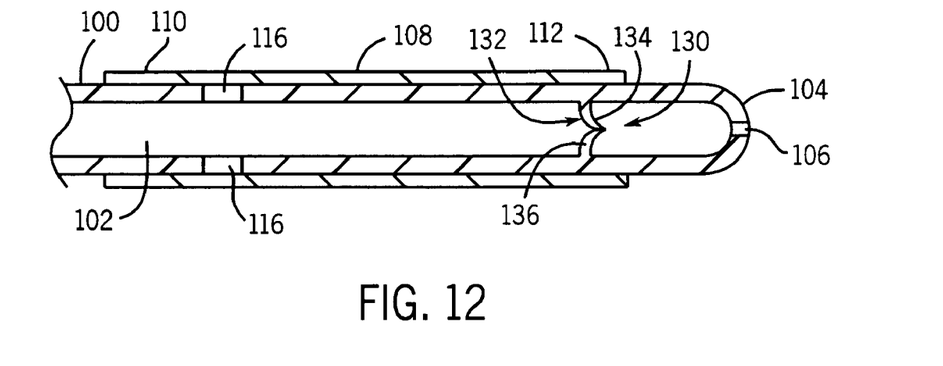
FIG. 12 is a view similar to FIG. 9, showing a fourth embodiment of the autoinflating, autoregulating balloon catheter assembly according to the invention with the balloon in the unexpanded or relaxed state.
Figure 13:
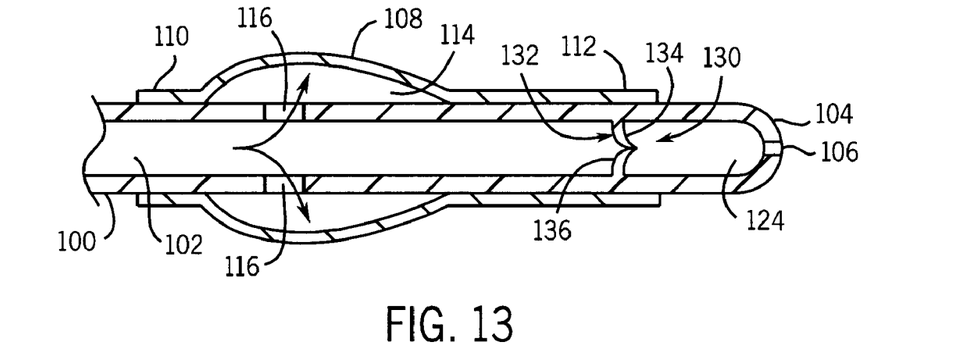
FIG. 13 is a view of the fourth embodiment similar to FIG. 10 showing the balloon in the partially expanded state.
Figure 14:
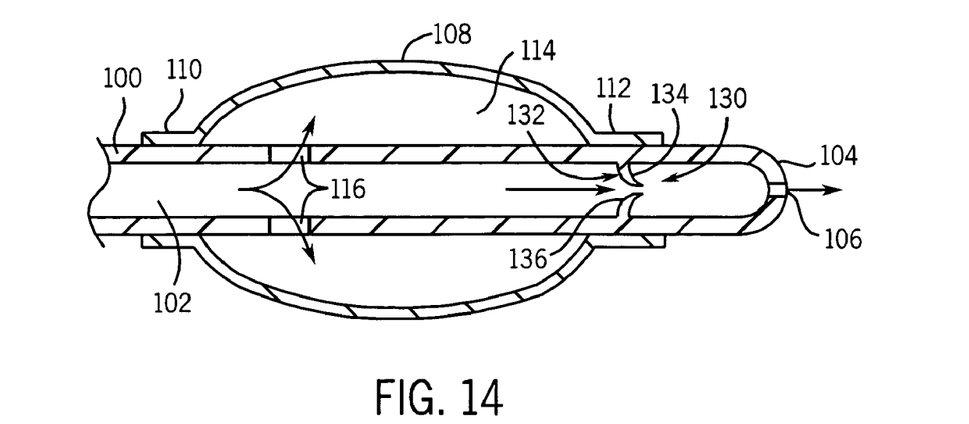
FIG. 14 is a view of the fourth embodiment similar to FIG. 11 showing the balloon in the fully expanded state.

A fourth embodiment of the autoregulating, autoinflation assembly according to the invention is seen in FIGS. 12-14. In this embodiment, the structure of the catheter is substantially the same as that of the third embodiment, and therefore identical reference numerals will be used. The primary distinction between the third and fourth embodiments lies in the structure of the internal valve means. In this embodiment, the internal valve means 130 comprises a duckbill valve 132 positioned intermediate the fluid outlet aperture 106 and the balloon inflation apertures 116. The duckbill valve 132 comprises a pair of tapered flanges 134, 136 which extend radially inwardly and distally. The flanges are tapered along the length so that the base of the flange is significantly broader than the tip. The structure of the flanges 134, 136 is dimensioned so that the ends of the flanges will not separate from one another until the pressure differential between the fluid on the interior of the catheter assembly and that on the exterior of the catheter assembly exceeds the predetermined fluid pressure differential. Once this pressure differential has been exceeded, fluid will deflect the tips of the tapered members radially outwardly to form an opening through the duckbill valve, thereby establishing fluid communication between the lumen 102 and the outlet aperture 106.

As in the earlier embodiments, the valve is adapted to automatically regulate the internal pressure inside the balloon 108 with varying fluid flow rates through the catheter assembly. For example, once the fluid pressure inside the balloon exceeds the predetermined fluid pressure differential, the duckbill valve 132 opens for the discharge of fluid from the catheter assembly. As the pressure continues to rise, the tapered flanges 134, 136 will continue to be deflected more and more radially outwardly, thereby enlarging the effective cross-sectional area of the fluid aperture through the valve. Similarly, as the pressure differential begins to drop, the elasticity of the flange members 134, 136 will draw the flange members toward one another, thereby reducing the effective opening of the fluid flow path through the catheter assembly. The dynamic response of the duckbill valve maintains the fluid pressure inside the balloon substantially constant for a wide range of fluid flow rates through the catheter assembly.

The autoinflating, autoregulating catheter assembly according to the invention is a significant improvement in preventing over-inflation of the balloon for a wide variety of fluid flow rates through the autoinflating catheter. Depending upon the particular design for the autoregulating structure, all or only a portion of the initial fluid pressure may be directed to inflating the balloon. Once the balloon has reached a desired inflation, a continued increase in fluid flow results in more fluid passing through the catheter assembly while maintaining the same relative level of balloon inflation. With this structure, potential tissue damage as a result of over-inflation of an autoinflated balloon is reduced.

While the invention has been particularly described in connection with certain specific embodiments thereof, it is to be understood that this is by way of illustration and not of limitation, and the scope of the appended claims should be construed as broadly as the prior art will permit.

What is claimed is:

1. A balloon catheter assembly comprising:
a catheter body having a first lumen extending from a proximal end thereof through at least a portion of the length of the catheter body, the catheter body being provided with a fluid discharge aperture for discharging fluid from the lumen;
a balloon secured to an exterior surface of the catheter body, the balloon being expandable between a relaxed state and an expanded state in response to a positive fluid pressure differential between the interior and the exterior of the lumen;
the catheter body being formed with at least one balloon inflation aperture fluidly interconnecting the lumen and the interior of the balloon such that fluid from the lumen can be received in the balloon through the at least one balloon inflation aperture so as to result in expansion of the balloon from the catheter body; and
an autoregulation valve provided on one of the balloon and the catheter body, the valve being adapted to restrict the flow of fluid through the fluid discharge aperture at fluid pressure differentials lower than a predetermined fluid pressure differential, and to expand a fluid flow path between the lumen and the fluid discharge aperture at pressure differential levels equal to or greater than the predetermined fluid pressure differential;
the first lumen providing fluid flow and fluid communication with the balloon by way of the balloon inflation aperture and to exit the catheter by way of the fluid discharge aperture,
wherein the autoregulation valve comprises a one-way valve including a valve seat provided within the catheter lumen proximally of the fluid discharge aperture, the seat being formed with a valve aperture therein in fluid communication with the lumen and having an internal diameter smaller than that of the lumen, a valve member disposed within the catheter lumen distally of the seat, and a valve spring disposed within the catheter lumen distally of the valve member and adapted to bias the valve member into seating engagement with the seat, the spring being selected to close the valve aperture at pressure levels within the lumen below the predetermined pressure differential, and to permit the valve to be lifted from engagement with the valve seat at pressure levels equal to or greater than the predetermined pressure differential, thereby opening the fluid discharge aperture to flow of fluid from the lumen.

2. A catheter assembly according to claim 1, wherein the bias of the spring is so selected that the valve member will not be lifted from the valve seat until the balloon has been inflated to a predetermined degree.

3. A catheter assembly according to claim 1, wherein the valve member comprises a ball.

4. A catheter assembly according to claim 3, wherein the valve seat is tapered so that the cross-sectional area of the valve aperture is greater at the distal end of the valve seat than the proximal end of the valve seat.

5. A catheter assembly, comprising:
a catheter;
a first lumen extending through the catheter;
a first fluid outlet aperture extending through a wall of the catheter to permit a fluid to exit the catheter assembly;
an internal valve in the lumen that is spaced proximally of the fluid outlet aperture, the internal valve configured to control flow of the fluid through the fluid outlet aperture; and
a balloon connected to the catheter, wherein the balloon is fluidly connected to the lumen through a second fluid outlet aperture of the wall of the catheter to allow inflation of the balloon by the fluid, the first lumen providing fluid flow and fluid communication with the balloon by way of the second fluid outlet aperture and to exit the catheter by way of the first fluid outlet aperture, wherein the internal valve prevents flow of the fluid from the lumen through the first fluid outlet aperture until the balloon has inflated to a predetermined degree and permits the flow of the fluid from the lumen through the second fluid outlet aperture when the balloon is inflated to the predetermined degree.

6. The catheter assembly of claim 5, wherein the balloon inflates at a predetermined fluid pressure differential between a first fluid pressure in the first lumen and a second fluid pressure on the exterior of the balloon.

7. The catheter assembly of claim 6, wherein the internal valve comprises a valve seat and a spring-biased ball biased toward the valve seat.

8. The catheter assembly of claim 7, wherein the ball is retracted from the valve seat when a fluid pressure differential between the first fluid pressure and the second fluid pressure exceeds the predetermined fluid pressure differential.

9. The catheter assembly of claim 8, wherein the valve seat is tapered whereby a fluid flow through the valve and out the first fluid outlet aperture increases as the fluid pressure differential increases.

10. The catheter assembly of claim 5, wherein the internal valve comprises a valve seat and a cone-shaped valve member biased toward the valve seat.

11. The catheter assembly of claim 5, wherein the balloon is fluidly connected to the first lumen by at least one balloon aperture extending through a wall of the catheter.

12. A method of performing retrograde cardioplegia solution perfusion, comprising the steps of:
providing a catheter assembly having a catheter and a balloon coupled to the catheter, the catheter having a first lumen extending there through;
providing a first fluid pathway from the first lumen into the balloon and a second fluid pathway from the first lumen out of the catheter assembly, wherein the first lumen provides fluid flow and fluid communication with the balloon by way of a balloon inflation aperture and to exit the catheter by way of a fluid discharge aperture;
providing an internal valve in the lumen that is spaced proximally of the fluid discharge aperture, the internal valve configured to control flow of a fluid through the second fluid pathway to the fluid discharge aperture;
inserting the catheter into a blood vessel;
inflating the balloon by supplying a cardioplegia solution through the first lumen and the balloon inflation aperture into the balloon;
after inflating the balloon to a predetermined degree, opening the second fluid pathway from the first lumen; and
perfusing the heart with the cardioplegia solution by continuing to supply the cardioplegia solution through the first lumen and through the fluid discharge aperture of the second fluid pathway while the balloon is inflated to the predetermined degree.

13. The method of claim 12, wherein the second fluid pathway increases in size as a supply pressure of the cardioplegia solution increases.

14. The method of claim 13, wherein the internal valve comprises a valve seat and a spring-biased ball.

15. The method of claim 12, wherein the catheter is inserted into a coronary sinus.

16. The method of claim 15, wherein the balloon occludes the coronary sinus when inflated.

* * * * *